United States Patent
Park et al.

(10) Patent No.: US 11,442,050 B2
(45) Date of Patent: Sep. 13, 2022

(54) ALUMINUM ION DETECTOR, METHOD OF MANUFACTURING THE SAME, AND ALUMINUM ION DETECTION METHOD USING THE SAME

(71) Applicant: Korea University Research and Business Foundation, Sejong Campus, Sejong-si (KR)

(72) Inventors: Jin Sung Park, Guri-si (KR); Gyu Do Lee, Namyangju-si (KR); Woong Kim, Gwangju (KR); Hyun Jun Park, Seoul (KR)

(73) Assignee: Korea University Research and Business Foundation, Sejong Campus, Sejong-si (KR)

(*) Notice: Subject to any disclaimer, the term of this patent is extended or adjusted under 35 U.S.C. 154(b) by 252 days.

(21) Appl. No.: 16/540,374

(22) Filed: Aug. 14, 2019

(65) Prior Publication Data
US 2020/0057036 A1    Feb. 20, 2020

(30) Foreign Application Priority Data
Aug. 14, 2018  (KR) .................. 10-2018-0094974

(51) Int. Cl.
*G01N 31/22*  (2006.01)
*G01N 21/78*  (2006.01)

(52) U.S. Cl.
CPC ............. *G01N 31/22* (2013.01); *G01N 21/78* (2013.01)

(58) Field of Classification Search
CPC .............. G01N 31/22; G01N 21/78; G01N 2021/8466; G01N 33/025; G01N 2021/825; B82Y 30/00
See application file for complete search history.

(56) References Cited

FOREIGN PATENT DOCUMENTS

| JP | 2012-047657 A | 3/2012 |
|---|---|---|
| KR | 10-2011-0081697 A | 7/2011 |
| KR | 10-1652643 B1 | 8/2016 |

OTHER PUBLICATIONS

Chen, Shan, et al. "Rapid visual detection of aluminium ion using citrate capped gold nanoparticles." Analyst 137.9 (2012): 2021-2023. (Year: 2012).*

Nigoghossian, Karina, et al. "Orange pectin mediated growth and stability of aqueous gold and silver nanocolloids." Applied Surface Science 341 (2015): 28-36. (Year: 2015).*

Kumar, Amit, and Ghanshyam S. Chauhan. "Extraction and characterization of pectin from apple pomace and its evaluation as lipase (steapsin) inhibitor." Carbohydrate Polymers 82.2 (2010): 454-459. (Year: 2010).*

Gawkowska, Diana, Justyna Cybulska, and Artur Zdunek. "Structure-related gelling of pectins and linking with other natural compounds: A review." Polymers 10.7 (2018): 762. (Year: 2018).*

* cited by examiner

*Primary Examiner* — Jennifer Wecker
*Assistant Examiner* — Oyeleye Alexander Alabi
(74) *Attorney, Agent, or Firm* — Sughrue Mion, PLLC

(57) ABSTRACT

Provided is an aluminum ion detector. The aluminum ion detector may include apple extracts having a predetermined concentration, and metal nano particles coupled to the apple extracts.

12 Claims, 21 Drawing Sheets
(16 of 21 Drawing Sheet(s) Filed in Color)

[Fig. 1]
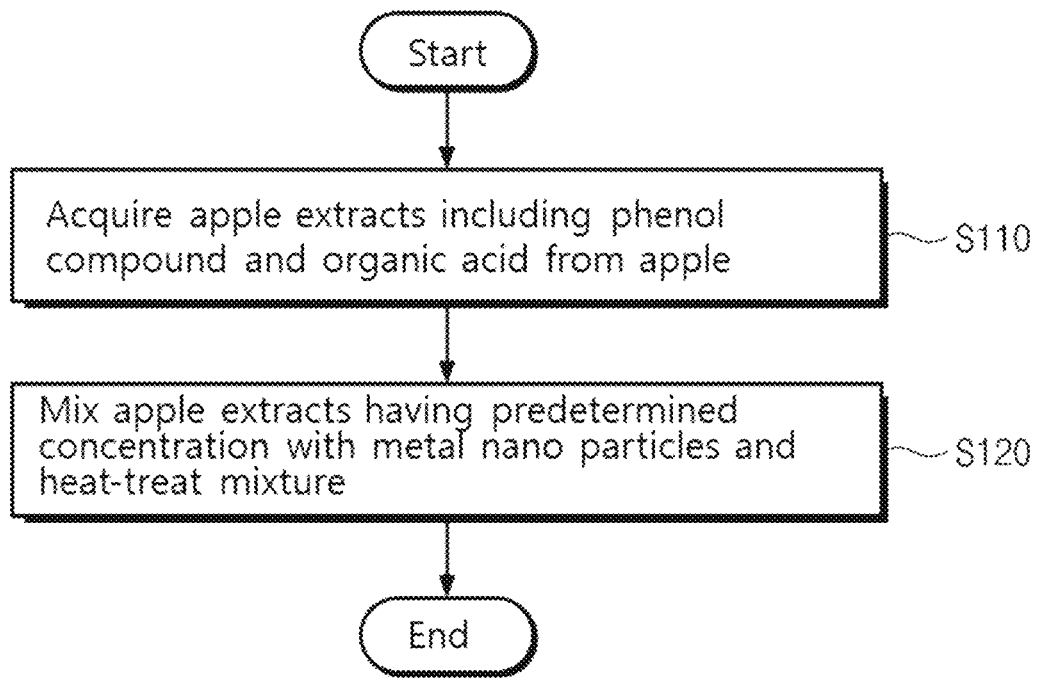

[Fig. 2]
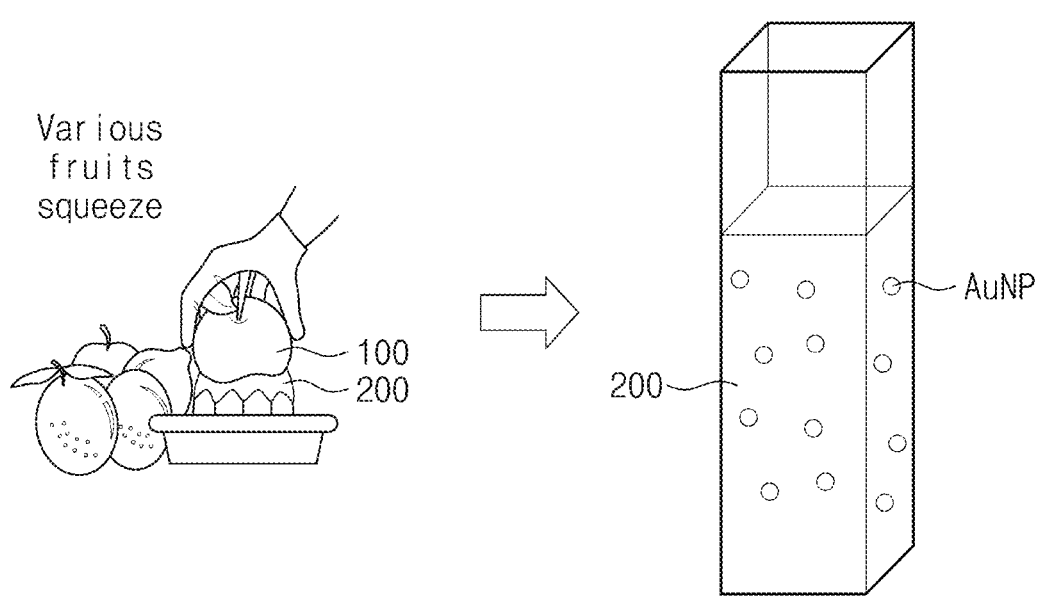

[Fig. 3]
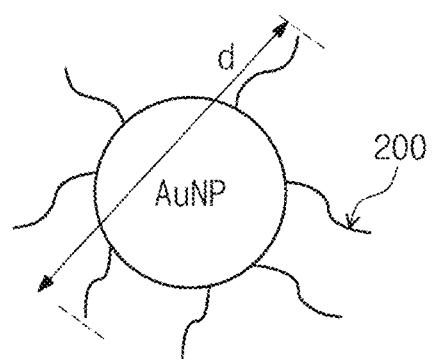

[Fig. 4]
(a)
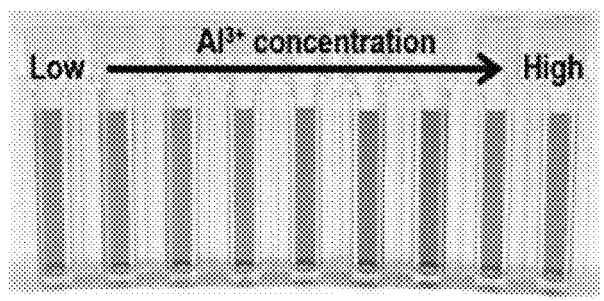
(b)
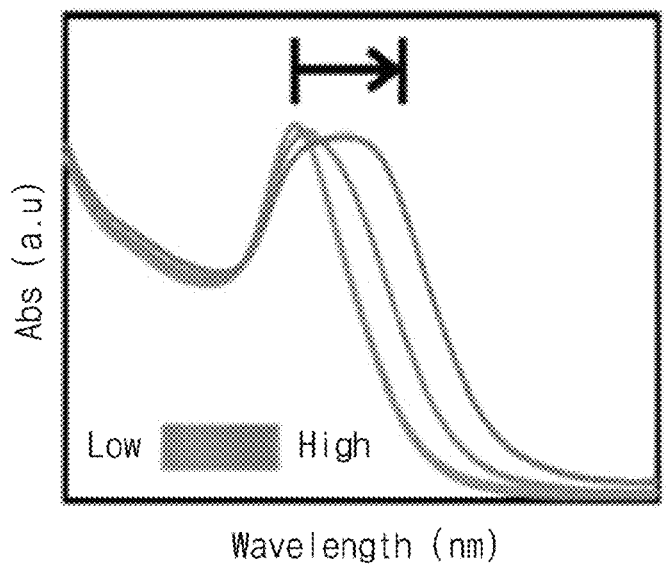

[Fig. 5]
(a)
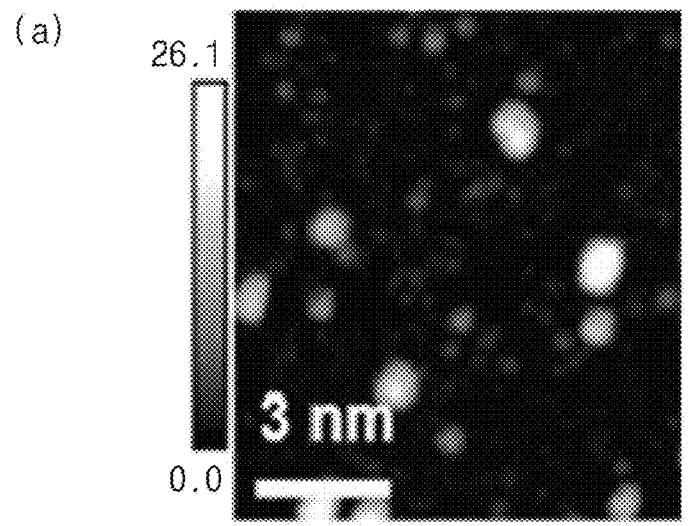
(b)
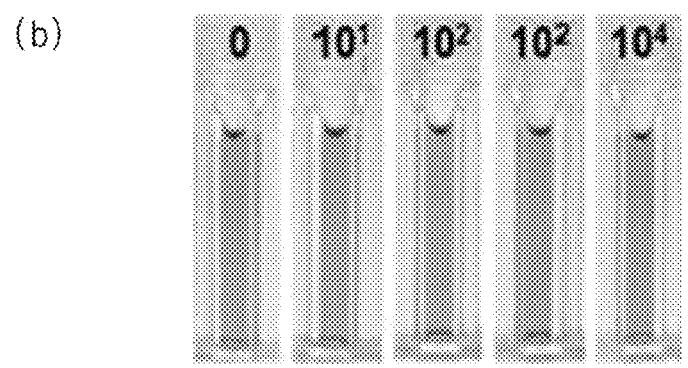
(c)
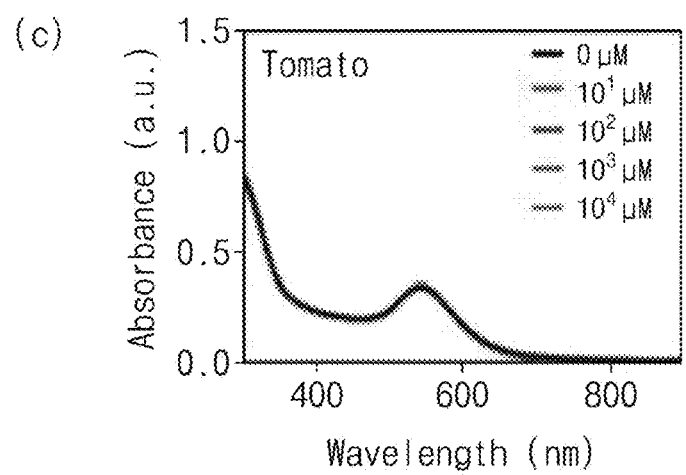

[Fig. 6]
(a)
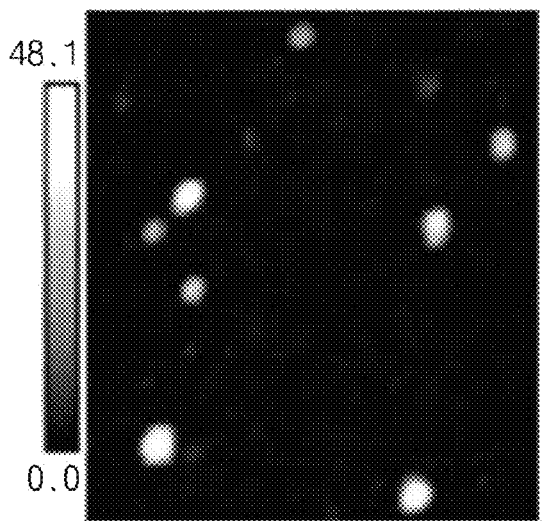
(b)
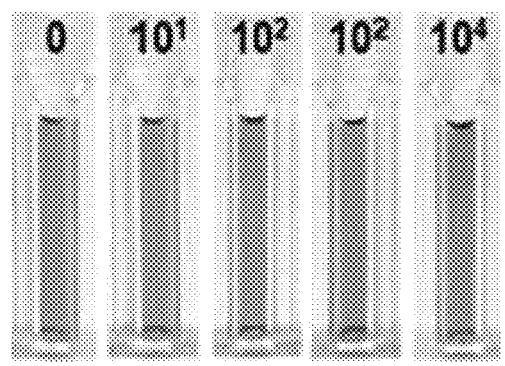
(c)
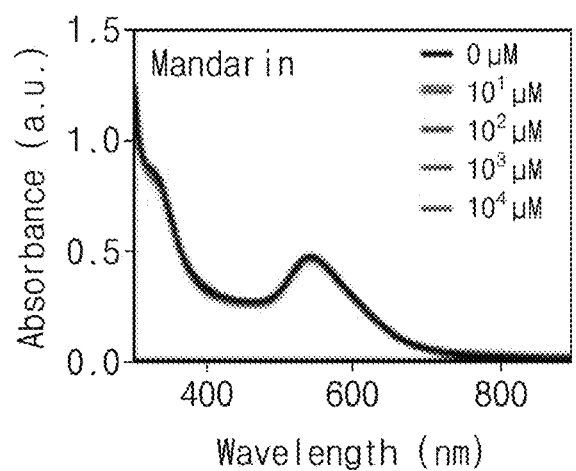

[Fig. 7]
(a)
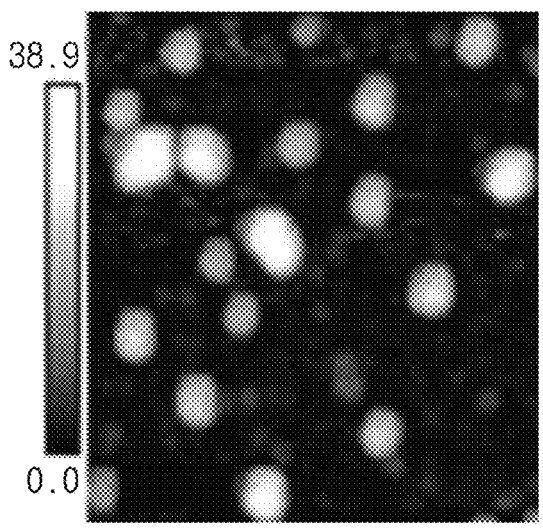
(b)
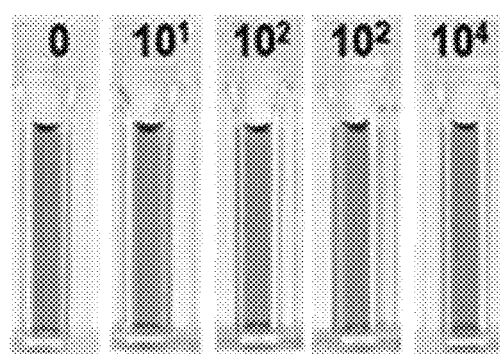
(c)
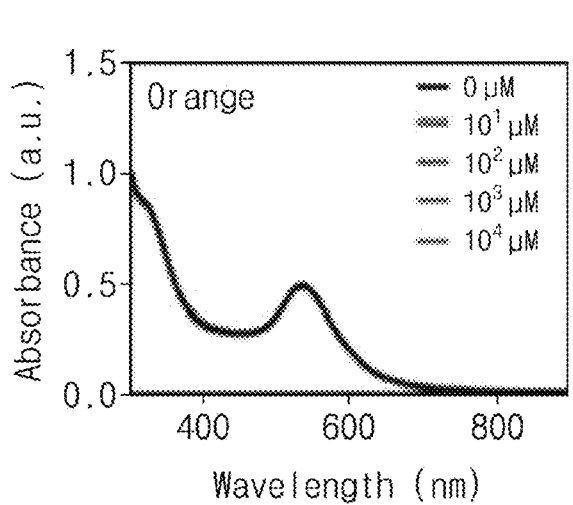

[Fig. 8]
(a)
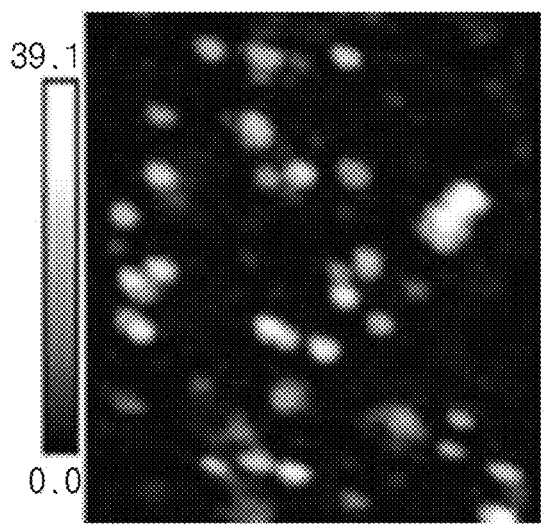
(b)
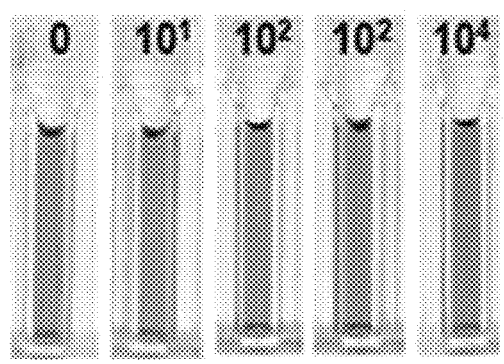
(c)
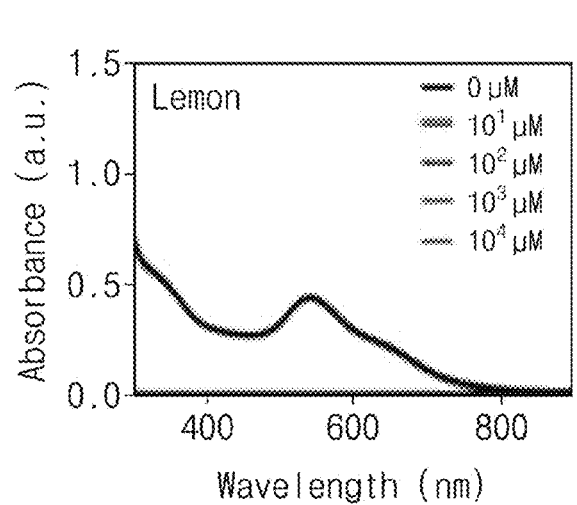

[Fig. 9]
(a)
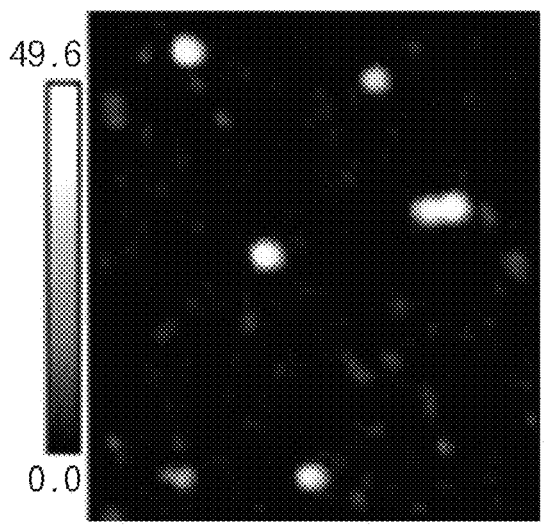
(b)
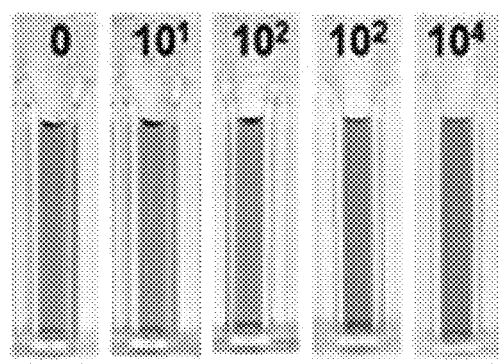
(c)
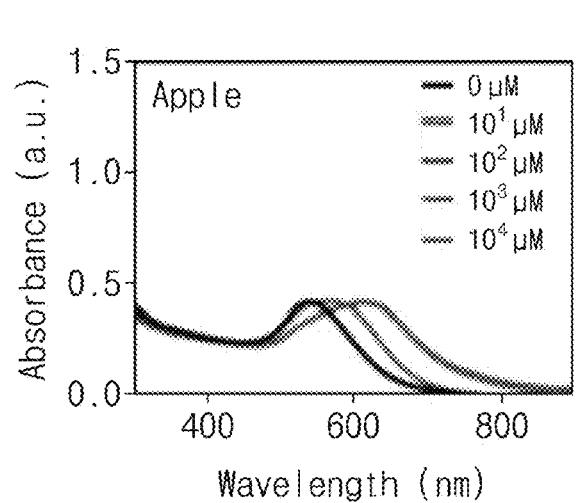

[Fig. 10]
(a)
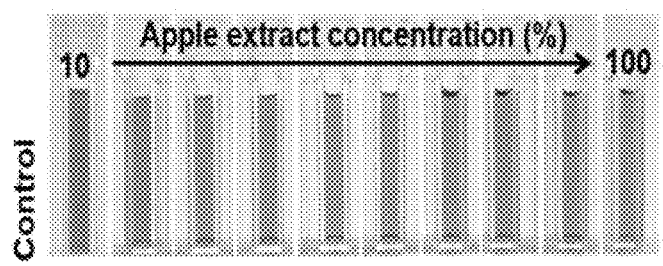
(b)
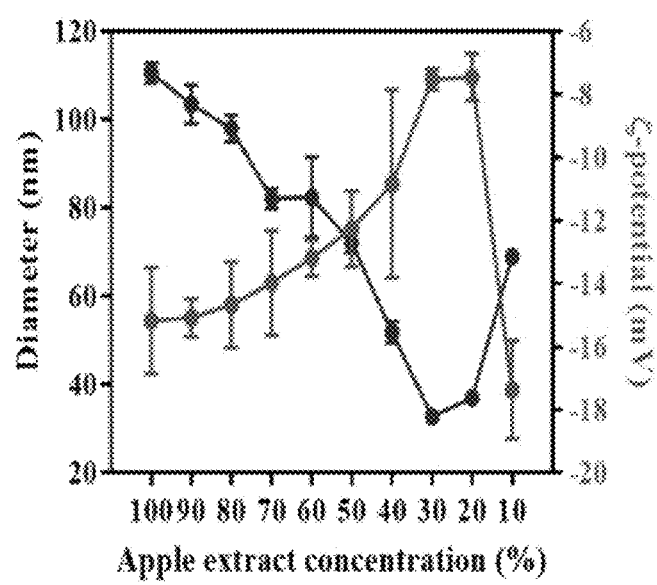

[Fig. 11]
(a)
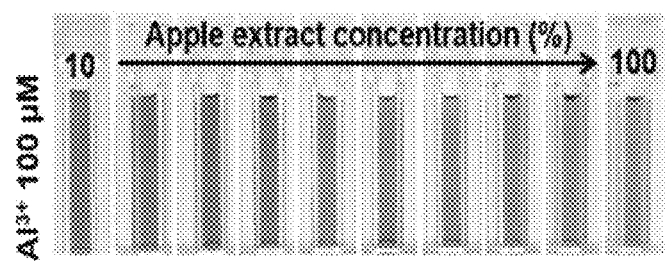
(b)
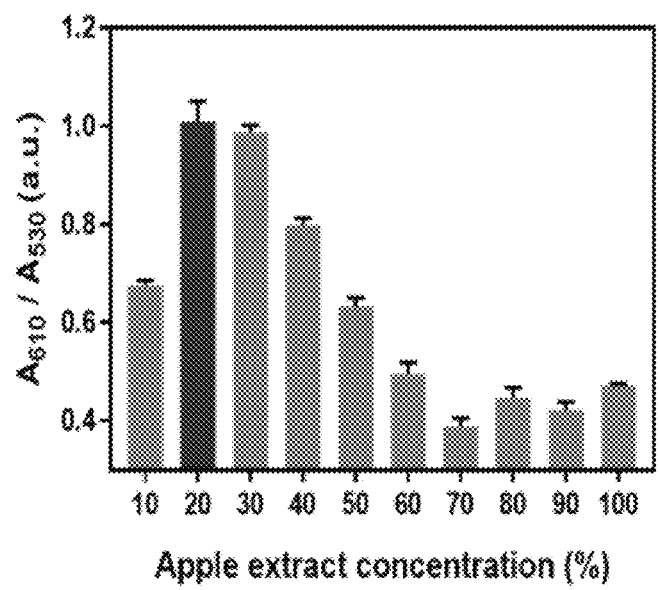

[Fig. 12]
(a)
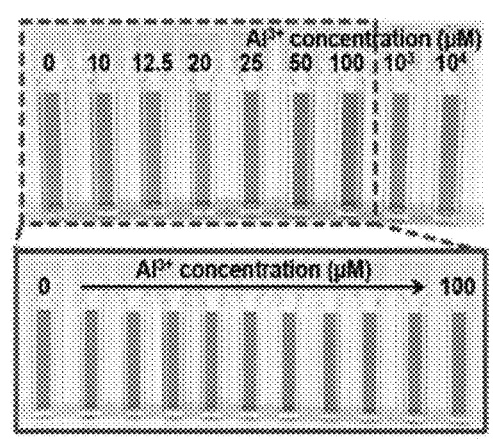
(b)
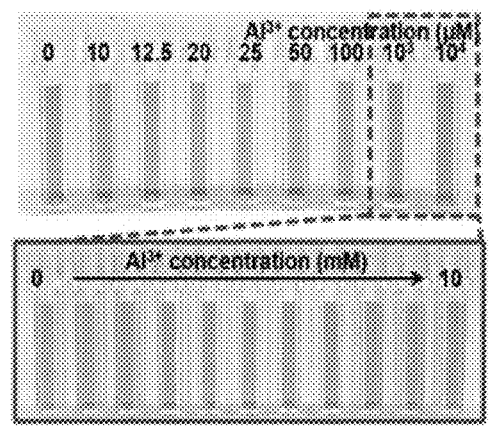

[Fig. 13]
(a)
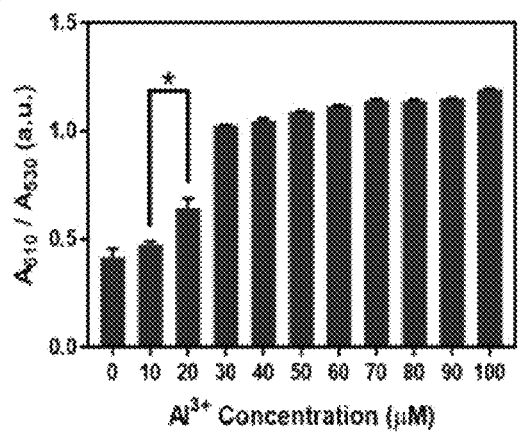
(b)
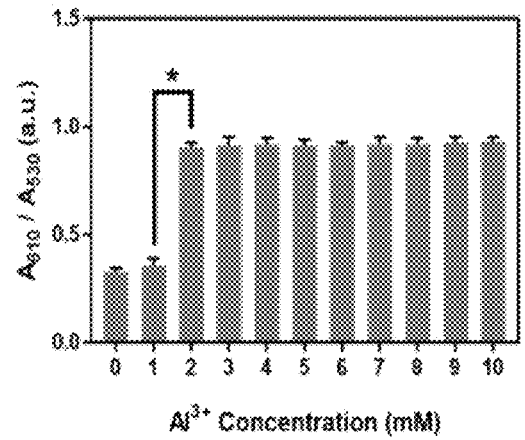

[Fig. 14]
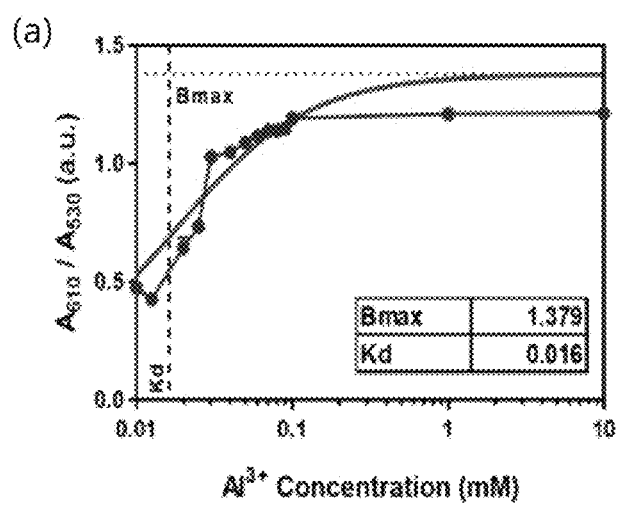
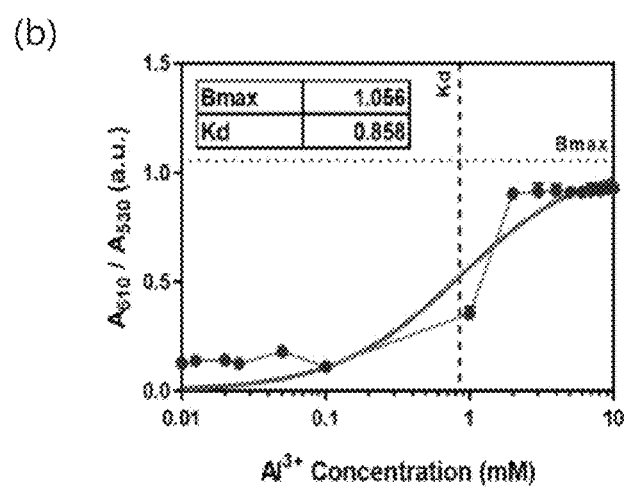

[Fig. 15]
(a)
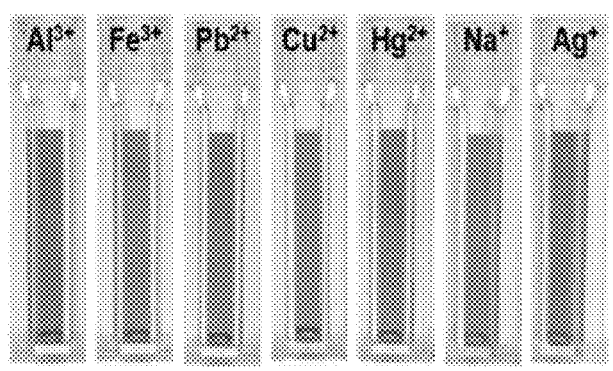
(b)
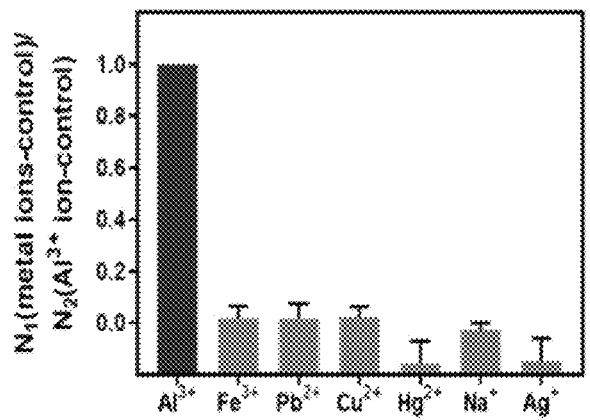

[Fig. 16]
(a)
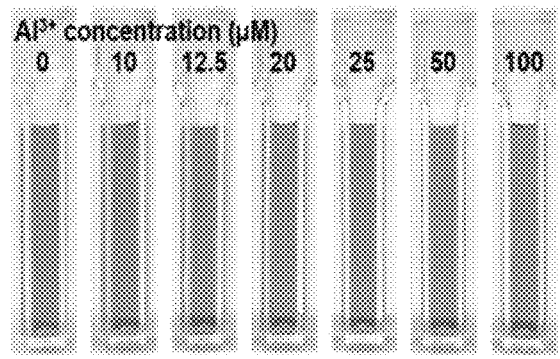
(b)
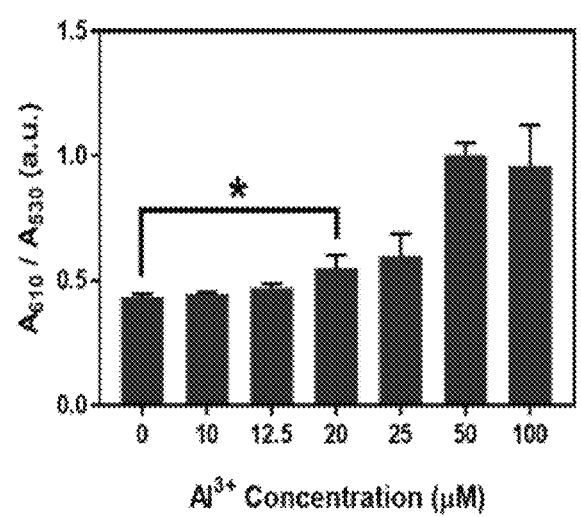

[Fig. 17]
(a)
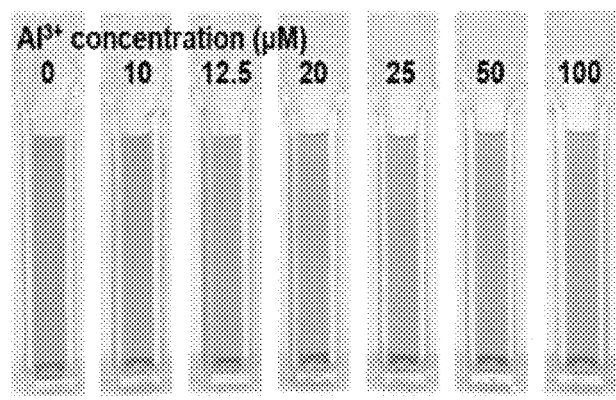
(b)
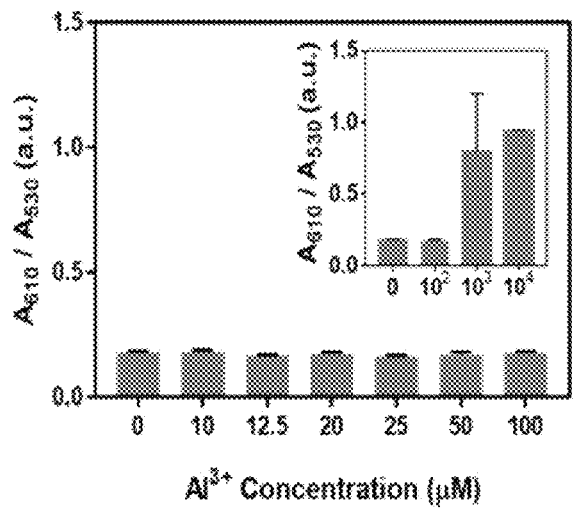

[Fig. 18]
(a)
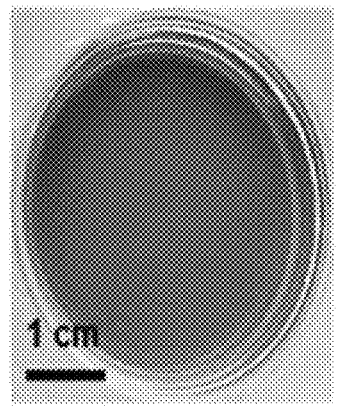
(b)
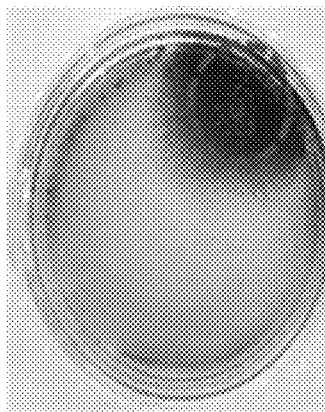

[Fig. 19]
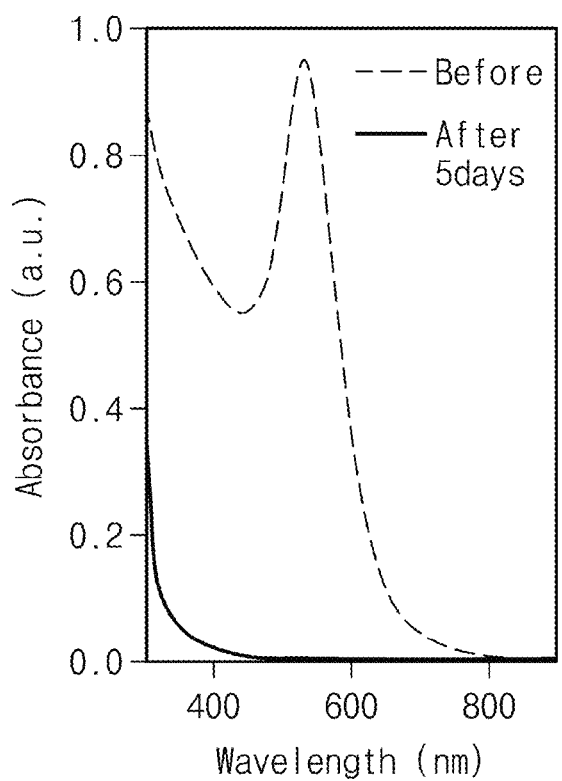

[Fig. 20]
(a)
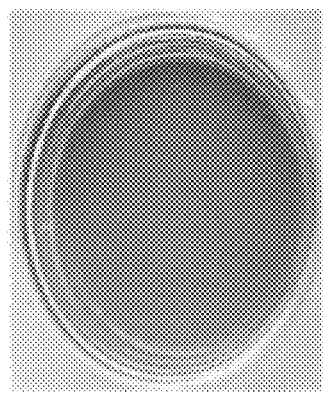
(b)
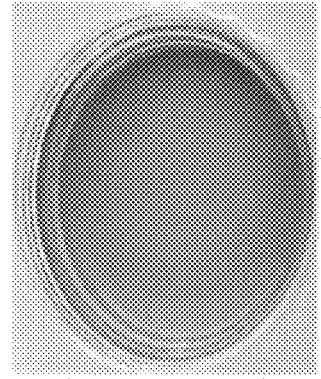

[Fig. 21]
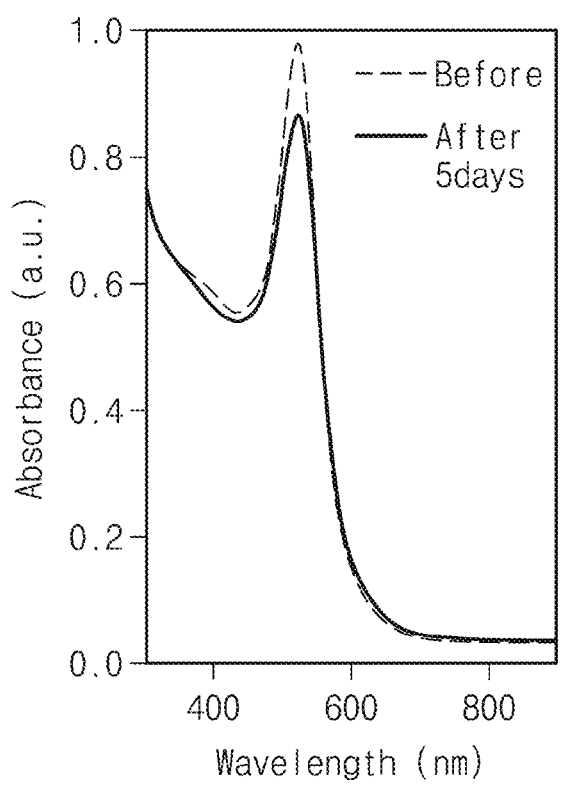

ALUMINUM ION DETECTOR, METHOD OF MANUFACTURING THE SAME, AND ALUMINUM ION DETECTION METHOD USING THE SAME

BACKGROUND OF THE INVENTION

1. Field of the Invention

The present invention relates to an aluminum ion detector, a method for manufacturing the same, and an aluminum ion detecting method using the same, and more particularly to an aluminum ion detector containing extracts of a fruit, a method for manufacturing the same, and an aluminum ion detecting method using the same.

2. Description of the Prior Art

Aluminum (Al) is a metal that is most abundant among various metals, and is most abundant among all elements, next to oxygen and silicon. Further, aluminum has been widely used in many industrial fields, such as automobile and computer manufacturing industries and medical fields. However, trivalent aluminum ions (Al3+) are known as a toxic material in a biochemical aspect.

High level of aluminum ions in a human body cause a severe damage to a neural system, including the Alzheimer's disease and the Parkinson's disease. Moreover, aluminum ions of a high concentration damage acidification of the earth and the aquatic environments. For example, because aluminum in the water restrains absorption of phosphor, it hampers growth of plants.

Accordingly, Environmental Protection Agency (EPA) strictly regulates the amount of aluminum ions in drinking water and surface water. For the reason, it is very important in an environmental aspect to detect aluminum ions of a low concentration in a solution. Although conventional methods using devices, for example, an inductively coupled plasma mass spectrometer (ICP-MS) and an atomic absorption spectrophotometer (AAS) have been still used to identify aluminum ions of a low level, the methods require expensive equipment and much time, and is is impossible to detect aluminum in real time. Accordingly, various technologies for efficiently detecting aluminum ions have been continuously researched and developed.

SUMMARY OF THE INVENTION

The present invention provides an aluminum ion detector having an improved sensitivity, a method for manufacturing the same, and an aluminum ion detecting method using the same.

The present invention provides an eco-friendly aluminum ion detector, a method for manufacturing the same, and an aluminum ion detecting method using the same.

The present invention provides an aluminum ion detector that can promptly detect aluminum ions, a method for manufacturing the same, and an aluminum ion detecting method using the same.

The technical objects of the present invention are not limited to the above-described ones.

In order to solve the technical problems, the present invention provides an aluminum ion detector.

According to an embodiment, the aluminum ion detector may include apple extracts having a predetermined concentration, and metal nano particles coupled to the apple extracts.

According to an embodiment, the apple extracts may include a phenol compound and an organic acid.

According to an embodiment, the phenol compound may include polyphenol, and the organic acid includes citrate.

According to an embodiment, color change characteristics may be provided according to whether the metal nano particles and aluminum ions are selectively reacted.

According to an embodiment, a predetermined concentration of the apple extracts may be defined as in Equation 1, and the color change characteristics according to the selective reaction with the aluminum ions may be controlled according to the predetermined concentration of the apple extracts, $$\text{Concentration} = (\text{volume of apple extracts})/(\text{volume of apple extracts} + \text{volume of distilled water}). \quad <\text{Equation 1}>$$

According to an embodiment, the predetermined concentration according to Equation 1 may be 20 wt % to 30 wt %.

According to an embodiment, the aluminum ion detector may be self-condensed.

According to an embodiment, the aluminum ion detector selectively may react with aluminum ions at a limit concentration of 20 µl or more.

According to an embodiment, the metal may be gold (Au).

According to an embodiment, the value of a total amount ($B_{max}$) peculiarly coupled to aluminum ions may be 1.379 or more.

According to an embodiment, the value of a concentration ($K_d$) reaching 50% of a total amount peculiarly coupled to aluminum ions may be 0.016 or less.

In order to solve the technical problems, the present invention provides a method for manufacturing an aluminum ion detector.

According to an embodiment, the method for manufacturing an aluminum ion detector may include acquiring apple extracts including a phenol compound and an organic acid from an apple, and mixing the apple extracts of a predetermined concentration with metal nano particles and heat-treating the mixture.

According to an embodiment, the metal nano particles may include gold nano particles.

In order to solve the technical problems, the present invention provides an aluminum ion detecting method using an aluminum ion detector.

According to an embodiment, the aluminum ion detecting method using an aluminum ion detector may include an aluminum ion reacting step of, in the aluminum ion detector including apple extracts including a phenol compound and an organic acid, and metal nano particles coupled to the apple extracts, causing aluminum ions to selectively react with the metal nano particles, and an aluminum ion detecting step of measuring a color change of the aluminum ion detector by using a reaction of the metal nano particles and the aluminum ions.

According to an embodiment, in the aluminum ion detecting step, a color change of an aluminum ion detecting probe is controlled according to a predetermined concentration of the apple extracts, and the predetermined concentration of the apple extracts is defined as in Equation 1, $$\text{Concentration} = (\text{volume of apple extracts})/(\text{volume of apple extracts} + \text{volume of distilled water}). \quad <\text{Equation 1}>$$

The aluminum ion detector according to the embodiment of the present invention may include the apple extracts having the predetermined concentration, and metal nano particles coupled to the apple extracts. Accordingly, the aluminum ion detector according to the embodiment of the present invention shows an improved sensitivity as compared with the existing aluminum ion detector so that aluminum ions of a lower concentration can be detected.

Further, the aluminum ion detector according to the embodiment is eco-friendly and can be self-condensed as it contains apple extracts. Accordingly, even after the aluminum ion detector is used for detection of aluminum, it can be easily post-processed (for example, a process of acquiring the aluminum ion detector to discard the aluminum ion detector).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features, and advantages of the present invention will be more apparent from the following detailed description taken in conjunction with the accompanying drawings, in which:

FIG. 1 is a flowchart illustrating a method for manufacturing an aluminum ion detector according to an embodiment of the present invention;

FIG. 2 is a view illustrating a process of manufacturing an aluminum ion detector according to the embodiment of the present invention;

FIG. 3 is a view illustrating an aluminum ion detector according to an embodiment of the present invention;

FIG. 4 is a picture and a graph for identifying color change characteristics of the aluminum ion detector according to the embodiment of the present invention;

FIGS. 5 to 9 are pictures and graphs for comparing aluminum ion detectors according to comparative examples and the embodiment of the present invention;

FIGS. 10 and 11 are a picture and a graph for comparing characteristics according to the concentration of apple extracts contained in the aluminum ion detector according to the embodiment of the present invention;

FIG. 12 is a picture for comparing color change characteristics of the aluminum ion detectors according to the embodiment and comparative example 1 of the present invention;

FIG. 13 is a graph for comparing detection limits of the aluminum ion detectors according to the embodiment and comparative example 1 of the present invention;

FIG. 14 is a graph for comparing the reaction rates of the aluminum ion detectors according to the embodiment and comparative example 1 of the present invention;

FIG. 15 is a picture and a graph illustrating selective coupling characteristics of the aluminum ion detector according to the embodiment of the present invention;

FIGS. 16 and 17 are pictures and graphs for comparing detection of aluminum in drinking water using the aluminum ion detectors according to the embodiment and comparative example 1 of the present invention;

FIG. 18 is a picture obtained by photographing self-condensation characteristics of the aluminum ion detector according to the embodiment of the present invention;

FIG. 19 is a graph for identifying the photographing self-condensation characteristics of the aluminum ion detector according to the embodiment of the present invention;

FIG. 20 is a picture obtained by photographing self-condensation characteristics of the aluminum ion detector according to comparative example 1 of the present invention; and FIG. 21 is a graph for identifying the photographing self-condensation characteristics of the aluminum ion detector according to comparative example 1 of the present invention.

DETAILED DESCRIPTION OF THE EXEMPLARY EMBODIMENTS

Hereinafter, preferred embodiments of the present invention will be described in detail with reference to the accompanying drawings. However, the technical spirit of the present invention is not limited to the embodiments, but may be realized in different forms. The embodiments introduced here are provided to sufficiently deliver the spirit of the present invention to those skilled in the art so that the disclosed contents may become thorough and complete.

When it is mentioned in the specification that one element is on another element, it means that the first element may be directly formed on the second element or a third element may be interposed between the first element and the second element. Further, in the drawings, the thicknesses of the films and the areas are exaggerated for efficient description of the technical contents.

Further, in the various embodiments of the present invention, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. Further, the terms "including" and "having" are used to designate that the features, the numbers, the steps, the elements, or combination thereof described in the specification are present, and may be understood that one or more other features, numbers, step, elements, or combinations thereof may be added. Further, in the specification, "connected to" is used to mean a plurality of elements are indirectly or directly connected to each other.

Further, in the following description of the present invention, a detailed description of known functions and configurations incorporated herein will be omitted when it may make the subject matter of the present invention rather unclear.

FIG. 1 is a flowchart illustrating a method of manufacturing an aluminum ion detector according to the embodiment of the present invention. FIG. 2 is a view illustrating a process of manufacturing an aluminum ion detector according to the embodiment of the present invention. FIG. 3 is a view illustrating an aluminum ion detector according to an embodiment of the present invention.

Referring to FIGS. 1 to 3, extracts 200 can be obtained from an apple 100 (S110). The apple extracts 200 may include a phenol compound and an organic acid. For example, the phenol compound may include polyphenol. The organic acid may include citrate. For example, as illustrated in FIG. 2, the apple extracts 200 can be obtained through a method of squeezing juice from the apple 100.

The aluminum ion detector according to the embodiment may be manufactured by mixing the apple extracts 200 with metal nano particles and heat-treating the mixture (S120). For example, the metal nano particles may be gold nano particles (AuNP). For example, the heat treatment temperature may be 80° C. to 100° C. According to the embodiment, in a step of manufacturing the aluminum ion detector, distilled water may be further provided. That is, the aluminum ion detector may be manufactured by mixing the apple extracts 200, the gold nano particles (AuNP), and the distilled water and heat-treating the mixture. According to the embodiment, before the apple extracts 200, the gold nano particles (AuNP), and the distilled water are mixed, the apple extracts 200 may be centrifugally separated. In detail, the apple extracts 200 may be mixed after being centrifugally separated for 20 minutes at a speed of 6,500 rpm.

According to an embodiment, as illustrated in FIG. 3, the aluminum ion detector may have a form in which the apple extracts 200 surround the circumference of the gold nano particles (AuNP).

The aluminum ion detector may provide color change characteristics according to whether a reaction with aluminum ions is selectively made. That is, the color of the aluminum ion detector may be changed when the metal nano particles react with aluminum ions. Accordingly, as a method for identifying a color change of the aluminum ion detector, it may be detected whether aluminum ions are present.

According to an embodiment, the aluminum ion detector may control the concentration of the apple extracts 200 such that the apple extracts 200 have a predetermined concentration. The predetermined concentration of the apple extracts 200 may be defined in Equation 1.

Concentration=(volume of apple extracts)/(volume of apple extracts+volume of distilled water). <Equation 1>

In detail, the predetermined concentration of the apple extracts 200 controlled according to Equation 1 may be 20 wt % to 30 wt %.

According to an embodiment, color change characteristics according to whether a selective reaction with aluminum ions is made may be controlled according to the predetermined concentration of the apple extracts 200. That is, when the predetermined concentration of the apple extracts 200 controlled according to Equation 1 is 20 wt % to 30 wt %, the sensitivity of the color change according to the selective reaction with the aluminum ions may be highest.

In detail, when the apple extracts 200 is controlled to have the predetermined concentration in the step of manufacturing the aluminum ion detector, the size (d) of the aluminum ion detector may be controlled. As illustrated in FIG. 3, the size (d) of the aluminum ion detector may be defined as the apple extracts 200 synthesized around the gold nano particles AuNP.

When the predetermined concentration of the apple extracts 200 controlled according to Equation 1 is 20 wt % to 30 wt %, the size of the aluminum ion detector may be smallest. As the size of the aluminum ion detector becomes smaller, the selective reaction with the aluminum ions are easily made, and accordingly, the color change may be easily made. Unlike the above description, when the predetermined concentration of the apple extracts 200 controlled according to Equation 1 is less than 20 wt % or more than 30 wt %, the size of the aluminum ion detector increases, and the sensitivity of the color change according to the selective reaction with the aluminum ions may be lowered.

According to an embodiment, the aluminum ion detector may be self-condensed. That is, as the aluminum ion detector contains the apple extracts 200, it may be self-condensed over time. Accordingly, with a method of, after waiting until the aluminum ion detectors that has been used are self-condensed, gathering and discarding the aluminum ion detectors in a condensation state, the aluminum ion detector may be easily post-processed.

Unlike this, in the case of the aluminum ion detector that does not contain the apple extracts 200, it may be difficult to remove the aluminum ion detector that has been used as the self-condensation characteristics do not occur. In this case, due to the toxic property of the gold nano particles (AuNP) themselves, a secondary damage to a human body or an environment may be caused.

According to an embodiment, the aluminum ion detector may selectively react with aluminum ions of a concentration of 20 μM or more and may show a meaningful color change. Further, the aluminum ion detector may include one, of which the value of a total amount ($B_{max}$), which is peculiarly coupled to aluminum ions, is 1.379 or more. Further, the aluminum ion detector may include one, of which the value of the concentration ($K_d$) reaching 50% of a total amount, which is peculiarly coupled to aluminum ions, is 0.016 or less. That is, the aluminum ion detector according to the embodiment may have a higher sensitivity as compared with an existing aluminum ion detector.

Until now, the aluminum ion detector and the method for manufacturing the same according to the embodiment of the present invention have been described. Hereinafter, an aluminum ion detecting method using the aluminum ion detector according to the embodiment of the present invention will be described.

The aluminum detecting method using the aluminum ion detector according to the embodiment may include an aluminum ion reacting step and an aluminum ion detecting step. Hereinafter, the steps will be described in detail. According to the embodiment, the aluminum ion detecting method may be performed by using the aluminum ion detector according to the embodiment described with reference to FIGS. 1 to 3.

In the aluminum ion reacting step, in the aluminum ion detector including apple extracts, and metal nano particles coupled to the apple extracts, aluminum ions may selectively react with the metal nano particles.

According to the embodiment, the apple extracts may include a phenol compound and an organic acid. For example, the phenol compound may include polyphenol. The organic acid may include citrate. The metal nano particles may include gold (Au) nano particles.

In the aluminum ion detecting step, a color change of the aluminum ion detector may be measured by the reaction of the metal nano particles and the aluminum ions. That is, it may be determined whether aluminum ions are present by measuring the color change of the aluminum ion detector.

According to the embodiment, the apple extracts contained in the aluminum ion detector may be controlled to a predetermined concentration. The predetermined concentration of the apple extracts may be defined in Equation 1.

Concentration=(volume of apple extracts)/(volume of apple extracts+volume of distilled water). <Equation 1>

In detail, the predetermined concentration of the apple extracts controlled according to Equation 1 may be 20 wt % to 30 wt %.

According to an embodiment, color change characteristics according to whether a selective reaction with aluminum ions is made may be controlled according to the predetermined concentration of the apple extracts. That is, when the predetermined concentration of the apple extracts controlled according to Equation 1 is 20 wt % to 30 wt %, the sensitivity of the color change according to the selective reaction with the aluminum ions may be highest. A more detailed description may be the same as a control of the concentration of the apple extracts 200 in the aluminum ion detector according to the embodiment described with reference to FIGS. 1 to 3, and the method for manufacturing the same. Accordingly, a detailed description will be omitted.

Until now, the aluminum ion detecting method using the aluminum ion detector according to the embodiment of the present invention has been described. Hereinafter, a detailed experimental example and a characteristic evaluation result of the aluminum ion detector according to the embodiment and the aluminum ion detecting method using the same will be described.

Manufacturing of Aluminum Ion Detector According to Embodiment

The aluminum ion detector according to the embodiment was manufactured by mixing 1 mL of $HAuCl_4$ of 1%, 1 mL of apple extracts, and 4 mL of distilled water and heat-treating the mixture at a temperature of 95° C. Apple extracts that were centrifugally separated for a time of 20 minutes at a speed of 6, 500 rpm before being mixed was used as the apple extracts. Further, the aluminum ion detector according to the embodiment was manufactured such that the concentration of the apple extracts according to Equation 1 is 20 wt %. (1 mL/1 mL+4 mL)

Manufacturing of Aluminum Ion Detector According to Comparative Example 1

The aluminum ion detector according to comparative example 1 was manufactured by mixing 1 mL of $HAuCl_4$ of a concentration of 1 wt %, 5 mL of Trisodium Citrate (TSC) of a concentration of 1 wt %, and 100 mL of distilled water and heat-treating the mixture at a temperature of 95° C.

Manufacturing of Aluminum Ion Detector According to Comparative Examples 2 to 5

The aluminum ion detector was manufactured through a method according to embodiment 1, and the aluminum ion detectors according to comparative examples 2 to 5 were manufactured by using tomato extracts, lemon extracts, citrus extracts, and orange extracts instead of apple extracts. The heat treatment temperature after the mixing was maintained to be the same as that of the method for manufacturing an aluminum ion detector according to comparative example 1, which has been described above.

The components of the aluminum ion detectors according to the embodiment and the comparative examples are summarized through Table 1.

TABLE 1

| Category | Configuration |
| --- | --- |
| Embodiment | $HAuCl_4$, apple extracts, distilled water |
| Comparative example 1 | $HAuCl_4$, Trisodium Citrate, distilled water |
| Comparative example 2 | $HAuCl_4$, tomato extracts, distilled water |
| Comparative example 3 | $HAuCl_4$, lemon extracts, distilled water |
| Comparative example 4 | $HAuCl_4$, citrus extracts, distilled water |
| Comparative example 5 | $HAuCl_4$, orange extracts, distilled water |

FIG. 4 is a picture and a graph for identifying color change characteristics of the aluminum ion detector according to the embodiment of the present invention.

Referring to FIG. 4A, a photo depicting a color change represented in the aluminum ion detector after the aluminum ion detector according to the embodiment differently reacted according to the concentrations of aluminum ions ($Al^{3+}$) is illustrated. Referring to FIG. 4B, a UV-vis spectroscopy after the aluminum ion detector according to the embodiment differently reacted according to the concentrations of aluminum ions ($Al^{3+}$) is illustrated. Low described in FIG. 4 means that the concentration of $Al^{3+}$ is low, and High means that the concentration of $Al^{3+}$ is high.

As can be seen from FIG. 4A, it could be identified that a color changes when the aluminum ion detector according to the embodiment reacts with aluminum ions $Al^{3+}$. Further, it could be identified that as the concentration of the reacted aluminum ions increases, the change of the color also becomes clear. As can be seen in FIG. 4B, it can be identified even from the wavelength change of the aluminum ion detector that when the aluminum ion detector according to the embodiment reacts with aluminum ions, the color changes.

FIGS. 5 to 9 are pictures and graphs for comparing aluminum ion detectors according to comparative examples and the embodiment of the present invention.

FIGS. 5 and 8 are pictures and graphs illustrating states and color change characteristics of the aluminum ion detectors according to comparative example 2, comparative example 3, comparative example 4, and comparative example 5 of the present invention. FIG. 9 is pictures and graphs illustrating states and color change characteristics of the aluminum ion detector according to the embodiment of the present invention. As of the drawings illustrate a picture of the aluminum ion detector of an AFM (Atomic Force Microscope), Bs of the drawings illustrate pictures illustrating color changes after the aluminum ion detector reacts with aluminum ions of concentrations of 0 μM, 10 μM, $10^2$ μM, $10^3$ μM, and $10^4$ μM, and Cs of the drawings illustrate UV-vis spectroscopies after the aluminum ion detector reacts with aluminum ions of concentrations of 0 μM, 10 μM, $10^2$ μM, $10^3$ μM, and $10^4$ μM.

As can be seen from FIGS. 5 to 8A, it can be identified that in the case of the aluminum ion detectors according to comparative example 2, comparative example 3, comparative example 4, and comparative example 5, the form of gold nano particles is identified but the sizes of the aluminum ion detectors and the states of the solutions differently appear according to the characteristics of the different fruits.

Further, as can be seen from FIGS. 5 to 8B and 8C, it can be identified that a color change does not appear after the reaction with the aluminum ions.

Meanwhile, as can be seen from FIG. 9A, gold nano particles are clearly observed in the aluminum ion detector according to the embodiment, and as can be seen from FIGS. 9A and 9C, it can be identified that a color change clearly appears after the reaction with aluminum ions.

That is, through FIGS. 5 to 9, it can be seen that when tomato, lemon, citrus, and orange extracts and the gold nano particles are coupled to each other to manufacture aluminum ion detectors, the aluminum ion detector cannot be used. However, it can be seen that it is particularly meaningful to use apple extracts among fruit extracts as gold nano particles are coupled to apple extracts in the aluminum ion detector according to the present invention, aluminum ions may be detected.

FIGS. 10 and 11 are a picture and a graph for comparing characteristics according to the concentration of apple extracts contained in the aluminum ion detector according to the embodiment of the present invention.

Referring to FIGS. 10 and 11, 10 aluminum ion detectors according to the embodiment, which contains different concentrations of apple extracts, are prepared. In the aluminum ion detectors, the concentrations of the apple extracts are 10 wt %, 20 wt, 30 wt %, 40 wt %, 50 wt %, wt %, 70 wt %, 80 wt %, 90 wt %, and 100 wt %. The concentrations of the apple extracts were differently manufactured through control of the amounts of apple extracts and the amounts of distilled water, which were mixed during a process of manufacturing the aluminum ion detector according to the embodiment, and are summarized through Table 2. All the heat treatment temperatures during the manufacturing process were maintained at 95° C.

TABLE 2

| Concentration (wt %) | Apple extracts (mL) | Distilled water (mL) | Total volume (mL) |
|---|---|---|---|
| 100 | 5 | 0 | 5 |
| 90 | 4.5 | 0.5 | 5 |
| 80 | 4 | 1 | 5 |
| 70 | 3.5 | 1.5 | 5 |
| 60 | 3 | 2 | 5 |
| 50 | 2.5 | 2.5 | 5 |
| 40 | 2 | 3 | 5 |
| 30 | 1.5 | 3.5 | 5 |
| 20 | 1 | 4 | 5 |
| 10 | 0.5 | 4.5 | 5 |

Referring to FIG. 10A, the aluminum ion detectors according to the embodiment, which contain apple extracts of different concentrations, are photographed. As can be seen in FIG. 10A, it could be identified that the aluminum ion detectors according to the embodiment were easily formed even when they contain apple extracts of different concentrations.

Referring to FIG. 10B, diameters and zeta potentials (ζ-potential, mV) were measured and illustrated for the aluminum ion detectors according to the embodiment, which contain apple extracts of different concentrations.

As can be seen in FIG. 10B, the aluminum ion detector according to the embodiment, which contained apple extracts of a concentration of 20 wt %, showed a diameter of about 35 nm and a zeta potential of about −8 mV. Further, the aluminum ion detector according to the embodiment, which contained apple extracts of a concentration of 30 wt %, showed a diameter of about 40 nm and a zeta potential of about −8 mV. That is, it could be identified that the aluminum ion detectors containing the concentrations of 20 wt % and 30 wt % showed significantly small sizes and significantly high zeta potentials as compared with the aluminum ion detectors containing apple extracts of different concentrations.

Referring to FIG. 11A, the color changes that appeared after the aluminum ion detectors according to the embodiment, which contained apple extracts of different concentrations, reacted with aluminum ions ($Al^{3+}$) having a concentration of 100 μM were photographed.

As can be seen in FIG. 11A, it could be identified that the aluminum ion detectors containing apple extracts of concentrations of 20 wt % and 30 wt % reacted with the aluminum ions of a concentration of 100 μM and showed a clear color change, but the aluminum ion detectors containing apple extracts of different concentrations did not show a clear color change.

Referring to FIG. 11B, a red shift ratio was derived after the aluminum ion detectors according to the embodiment, which contained apple extracts of different concentrations, were reacted with aluminum ions ($Al^{3+}$) having a concentration of 100 μM. The red shift ratio was derived by measuring an absorbance at a wavelength of 610 nm and an absorbance ratio ($A_{610}/A_{530}$, a.u.) at a wavelength of 530 nm. Further, the higher red shift ratio means a larger color change.

As can be seen in FIG. 11B, it could be identified that the red shift ratio is the highest in the aluminum ion detector containing apple extracts of a concentration of 20 wt %. Further, it could be identified that the aluminum ion detectors containing the concentrations of 20 wt % and 30 wt % showed significantly high red shift ratios as compared with the aluminum ion detectors containing apple extracts of different concentrations. That is, it could be identified that the aluminum ion detectors containing the concentrations of 20 wt % and 30 wt % showed high color change characteristics as compared with the aluminum ion detectors containing apple extracts of different concentrations.

As can be seen through FIGS. 10 and 11, it could be identified that the color change characteristics of the aluminum ion detectors according to the embodiment were controlled according to a predetermined concentration of the apple extracts. In particular, it can be seen that the concentration of the apple extracts has to be controlled to 20 wt % to 30 wt %. The predetermined concentration of the apple extracts may be defined in Equation 1.

Concentration=(volume of apple extracts)/(volume of apple extracts+volume of distilled water). <Equation 1>

FIG. 12 is a picture for comparing color change characteristics of the aluminum ion detectors according to the embodiment and comparative example 1 of the present invention.

Referring to FIG. 12A, after reacting with aluminum ions ($Al^{3+}$) having various concentrations, the aluminum ion detector according to the embodiment was photographed. As can be seen in FIG. 12A, it could be identified that the aluminum ion detector according to the embodiment showed a meaningful color change even when it reacted with aluminum ions of a concentration of 20 μM.

Referring to FIG. 12B, after reacting with aluminum ions ($Al^{3+}$) having various concentrations, the aluminum ion detector according to comparative example 1 was photographed. As can be seen in FIG. 12B, it could be identified that the aluminum ion detector according to comparative example 1 showed a meaningful color change even when it reacted with aluminum ions of a concentration of 20 m.

FIG. 13 is a graph for comparing detection limits of the aluminum ion detectors according to the embodiment and comparative example 1 of the present invention.

Referring to FIG. 13A, after the aluminum ion detector according to the embodiment reacts with aluminum ions ($Al^{3+}$) having various concentrations, a UV-vis spectroscopy absorption analysis result was derived. In order to identify a detection limit, *p-value was set to less than 0.0005. As can be seen in FIG. 13A, it can be identified that a limit concentration at which the aluminum ion detector according to the embodiment may detect aluminum ions ($Al^{3+}$) is 20 μM.

Referring to FIG. 13B, after the aluminum ion detector according to comparative example 1 reacts with aluminum ions ($Al^{3+}$) having various concentrations, a UV-vis spectroscopy absorption analysis result was derived. In order to identify a detection limit, *p-value was set to less than 0.0001. As can be seen in FIG. 13B, it can be identified that a limit concentration at which the aluminum ion detector according to comparative example 1 may detect aluminum ions ($Al^{3+}$) is 20 mM.

FIG. 14 is a graph for comparing the reaction rates of the aluminum ion detectors according to the embodiment and comparative example 1 of the present invention.

Referring to FIG. 14A, after the aluminum ion detector according to the embodiment reacts with aluminum ions ($Al^{3+}$) having various concentrations, a nonlinear fitting (hyperbola) analysis result for a UV-vis analysis result was derived. As can be seen in FIG. 14A, it could be identified that the value of $B_{max}$ (a value representing a total amount of peculiar coupling) of the aluminum ion detector according to the embodiment was 1.379, and the value of $K_d$ (the value representing the concentration reaching 50% of the total amount of the peculiar coupling) was 0.016.

Referring to FIG. 14B, after the aluminum ion detector according to comparative example 1 reacts with aluminum ions ($Al^{3+}$) having various concentrations, a nonlinear fitting (hyperbola) analysis result for a UV-vis analysis result was derived. As can be seen in FIG. 14B, it could be identified that the value of $B_{max}$ (a value representing a total amount of peculiar coupling) of the aluminum ion detector according to the embodiment was 1.056, and the value of $K_d$ (the value representing the concentration reaching 50% of the total amount of the peculiar coupling) was 0.858. That is, it can be seen that as compared with the aluminum ion detector according to comparative example 1, the aluminum ion detector according to the embodiment may have a better reaction rate with aluminum and may detect aluminum of a lower concentration.

As a result, through FIGS. 12 to 14, it can be seen that the aluminum ion detector according to the embodiment of the present invention showed an improved sensitivity and could detect aluminum ions of a lower concentration as compared with an existing aluminum ion detector. In detail, it can be seen that the limit concentration at which the existing aluminum ion detector may detect aluminum ions was 20 mM, but the limit concentration at which the aluminum ion detector according to the embodiment may detect aluminum ions is 20 μm and has a remarkably improved (a difference of about 1000 times from the limit concentration) sensitivity.

FIG. 15 is a picture and a graph illustrating selective coupling characteristics of the aluminum ion detector according to the embodiment of the present invention.

Referring to FIG. 15A, after the aluminum ion detector according to the embodiment reacted with aluminum ions ($Al^{3+}$), iron ions ($Fe^{3+}$), lead ions ($Pb^{2+}$), copper ions ($Cu^{2+}$), mercury ions ($Hg^{2+}$), sodium ions ($Na^+$), and silver ions ($Ag^+$), the color changes that appear in the aluminum ion detector were photographed.

Referring to FIG. 15A, it could be identified that the aluminum ion detector according to the embodiment showed a meaningful color change even when it reacted with aluminum ions ($Al^{3+}$), but it did not show a meaningful color change when reacting with iron ions ($Fe^{3+}$), lead ions ($Pb^{2+}$), copper ions ($Cu^{2+}$), mercury ions ($Hg^{2+}$), sodium ions ($Na^+$), and silver ions ($Ag^+$).

Referring to FIG. 15B, after the aluminum ion detector according to the embodiment reacted with aluminum ions ($Al^{3+}$), iron ions ($Fe^{3+}$), lead ions ($Pb^{2+}$), copper ions ($Cu^{2+}$), mercury ions ($Hg^{2+}$), sodium ions ($Na^+$), and silver ions ($Ag^+$), an analysis was made with a UV-vis spectroscopy and standardized.

As can be seen in FIG. 15B, it can be identified that when the aluminum ion detector according to the embodiment reacted with iron ions ($Fe^{3+}$), lead ions ($Pb^{2+}$), copper ions ($Cu^{2+}$), mercury ions ($Hg^{2+}$), sodium ions ($Na^+$), and silver ions (AO, the efficiency was at most less than 10%.

That is, through FIG. 15, it can be seen that the aluminum ion detector according to the embodiment of the present invention selectively reacts with aluminum ions ($Al^{3+}$).

FIGS. 16 and 17 are pictures and graphs for comparing detection of aluminum in drinking water using the aluminum ion detectors according to the embodiment and comparative example 1 of the present invention.

Referring to FIG. 16A, after the aluminum ion detector according to the embodiment reacts with drinking water including aluminum ions of a concentration of 0 μM, drinking water including aluminum ions of a concentration of 10 μM, drinking water including aluminum ions of a concentration of 12.5 μM, drinking water including aluminum ions of a concentration of 20 μM, drinking water including aluminum ions of a concentration of 25 μM, drinking water including aluminum ions of a concentration of 50 μM, and drinking water including aluminum ions of a concentration of 100 μM, it was photographed. As can be seen in FIG. 16A, it could be identified that when the aluminum ion detector according to the embodiment reacts with drinking water that does not contain aluminum, a meaningful color change that may be distinguished by naked eyes did not appear.

Referring to FIG. 16B, after the aluminum ion detector according to the embodiment reacted with drinking water including aluminum ions of a concentration of 0 μM, drinking water including aluminum ions of a concentration of 10 μM, drinking water including aluminum ions of a concentration of 12.5 μM, drinking water including aluminum ions of a concentration of 20 μM, drinking water including aluminum ions of a concentration of 25 μM, drinking water including aluminum ions of a concentration of 50 μM, and drinking water including aluminum ions of a concentration of 100 μM, UV-vis spectroscopy absorption analysis results for them were derived.

As can be seen in FIG. 16B, it could be identified that a color change that may be identified by naked eyes in FIG. 16A is not large, but the color change may be detected when the aluminum ion detector reacted with drinking water containing aluminum ions of a concentration of 20 μM or more through the UV-vis spectroscopy absorption analysis results.

Referring to FIGS. 17A and 17B, after the aluminum ion detector according to comparative example 1 reacted with drinking water including aluminum ions of a concentration of 0 μM, drinking water including aluminum ions of a concentration of 10 μM, drinking water including aluminum ions of a concentration of 12.5 μM, drinking water including aluminum ions of a concentration of 20 μM, drinking water including aluminum ions of a concentration of 25 μM, drinking water including aluminum ions of a concentration of 50 μM, and drinking water including aluminum ions of a concentration of 100 μM, they were photographed and are illustrated in FIG. 17A. Further, the UV-vis spectroscopy absorption analysis results were derived and are illustrated in FIG. 17B.

As can be seen in FIGS. 17A and 17B, it could be identified that in the aluminum ion detector according to comparative example 1, a meaningful color change that may be identified by naked eyes did not appear even in drinking water containing aluminum ions of a concentration of 100 μM and a reaction did not occur in the UV-vis spectroscopy absorption analysis results.

FIG. 18 is a picture obtained by photographing self-condensation characteristics of the aluminum ion detector according to the embodiment of the present invention. FIG. is a graph for identifying the photographing self-condensation characteristics of the aluminum ion detector according to the embodiment of the present invention.

Referring to FIGS. 18A and 18B, in order to identify condensation characteristics of the aluminum ion detector according to the embodiment, a picture photographed immediately after the aluminum ion detector according to the embodiment was manufactured is illustrated in FIG. 18A, and a picture photographed after the aluminum ion detector is left for five days at room temperature is illustrated in FIG. 18B.

As can be seen in FIGS. 18A and 18B, it could be identified that the aluminum ion detector according to the embodiment was self-condensed over time. Accordingly, it is easy to separate and retrieve the aluminum ion detector after the aluminum ion detector is used to detect aluminum ions. Further, it could be identified that bacteria were grown up in the aluminum ion detector according to the embodiment. Through this, it could be determined that the aluminum ion detector is eco-friendly as the bacteria were grown up.

Referring to FIG. 19, absorbance a.u. according to wavelengths (nm) for the aluminum ion detectors in the states of FIGS. 18A and 18B is shown. As can be seen in FIG. 19, it could be identified that an absorbance band disappears over time in the aluminum ion detector according to the embodiment. Through this, it is determined that the phenomenon is caused because the aluminum ion detector is self-condensed over time.

FIG. 20 is a picture obtained by photographing self-condensation characteristics of the aluminum ion detector according to comparative example 1 of the present invention. FIG. 21 is a graph for identifying the photographing self-condensation characteristics of the aluminum ion detector according to comparative example 1 of the present invention.

Referring to FIGS. 20A and 20B, in order to identify condensation characteristics of the aluminum ion detector according to comparative example 1, a picture photographed immediately after the aluminum ion detector according to comparative example 1 was manufactured is illustrated in FIG. 20A, and a picture photographed after the aluminum ion detector is left for five days at room temperature is illustrated in FIG. 20B. As can be seen in FIGS. 20A and 20B, it could be identified that the shape of the aluminum ion detector according to comparative example 1 was maintained constantly even if time elapses. Accordingly, it can be seen that the aluminum ion detector according to comparative example 1 is not self-condensed.

Referring to FIG. 21, absorbance a.u. according to wavelengths (nm) for the aluminum ion detectors in the states of FIGS. 20A and 20B is shown. As can be seen in FIG. 21, it could be identified that an absorbance band substantially coincides even if time elapses in the aluminum ion detector according to the embodiment. It is determined that this is because the shape of the aluminum ion detector according to comparative example 1 is constantly maintained in spite that time elapses.

The aluminum ion detector according to the embodiment of the present invention may include the apple extracts having the predetermined concentration, and metal nano particles coupled to the apple extracts. Accordingly, the aluminum ion detector according to the embodiment of the present invention shows an improved sensitivity as compared with the existing aluminum ion detector so that aluminum ions of a lower concentration can be detected.

Further, the aluminum ion detector according to the embodiment is eco-friendly and can be self-condensed as it contains apple extracts. Accordingly, even after the aluminum ion detector is used for detection of aluminum, it can be easily post-processed (for example, a process of acquiring the aluminum ion detector to discard the aluminum ion detector).

Although the preferred embodiments of the present invention have been described in detail until now, the scope of the present invention is not limited to the embodiments and should be construed by the attached claims. Further, it should be understood that those skilled in the art to which the present invention pertains may variously correct and modify the present invention without departing from the scope of the present invention.

What is claimed is:

1. An aluminum ion detector comprising:
    apple extracts having a predetermined concentration; and
    metal nano particles coupled to the apple extracts,
    wherein the predetermined concentration is 20 wt % to 30 wt %,
    wherein the aluminum ion detector selectively reacts with aluminum ions at a limit concentration of 20 μM or more, and
    wherein the value of a total amount ($B_{max}$) peculiarly coupled to aluminum ions is 1.379 or more.

2. The aluminum ion detector of claim 1, wherein the apple extracts comprise a phenol compound and an organic acid.

3. The aluminum ion detector of claim 2, wherein the phenol compound comprises polyphenol, and the organic acid comprises citrate.

4. The aluminum ion detector of claim 1, wherein color change characteristics are provided according to whether the metal nano particles and aluminum ions are selectively reacted.

5. The aluminum ion detector of claim 4, wherein a predetermined concentration of the apple extracts is defined as in Equation 1, and the color change characteristics according to the selective reaction with the aluminum ions are controlled according to the predetermined concentration of the apple extracts, Concentration=(volume of apple extracts)/(volume of apple extracts+volume of distilled water).    <Equation 1>

6. The aluminum ion detector of claim 1, wherein the aluminum ion detector is self-condensed.

7. The aluminum ion detector of claim 1, wherein the metal is gold (Au).

8. The aluminum ion detector of claim 1, wherein the value of a concentration ($K_d$) reaching 50% of a total amount peculiarly coupled to aluminum ions is 0.016 or less.

9. A method for manufacturing the aluminum ion detector of claim 1, the method comprising:
    acquiring apple extracts comprising a phenol compound and an organic acid from an apple; and
    mixing the apple extracts of a predetermined concentration with metal nano particles and heat-treating the mixture, wherein the predetermined concentration is 20 wt % to 30 wt %.

10. The method of claim 9, wherein the metal nano particles comprise gold nano particles.

11. An aluminum ion detecting method using the aluminum ion detector of claim 1, comprising:
    an aluminum ion reacting step of, in the aluminum ion detector comprising apple extracts comprising a phenol compound and an organic acid, and metal nano particles coupled to the apple extracts, causing aluminum ions to selectively react with the metal nano particles; and an aluminum ion detecting step of measuring a color change of the aluminum ion detector by using a reaction of the metal nano particles and the aluminum ions.

12. The aluminum ion detecting method of claim 11, wherein in the aluminum ion detecting step, a color change of an aluminum ion detecting probe is controlled according to a predetermined concentration of the apple extracts, and the predetermined concentration of the apple extracts is defined as in Equation 1, $$\text{Concentration} = (\text{volume of apple extracts})/(\text{volume of apple extracts} + \text{volume of distilled water}). \quad \text{<Equation 1>}$$

* * * * *